(12) United States Patent
Bourget

(10) Patent No.: US 8,588,932 B2
(45) Date of Patent: Nov. 19, 2013

(54) COMMUNICATION BETWEEN A MEDICAL DEVICE AND A LEAD-BORNE DEVICE

(75) Inventor: Duane Bourget, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1413 days.

(21) Appl. No.: 12/042,813

(22) Filed: Mar. 5, 2008

(65) Prior Publication Data

US 2009/0228071 A1    Sep. 10, 2009

(51) Int. Cl.
*A61N 1/08*    (2006.01)
(52) U.S. Cl.
USPC ............................................. 607/116
(58) Field of Classification Search
USPC ............................................. 607/116
See application file for complete search history.

(56) References Cited

U.S. PATENT DOCUMENTS

| | | |
|---|---|---|
| 4,628,934 A | 12/1986 | Pohndorf et al. |
| 5,325,870 A | 7/1994 | Kroll et al. |
| 5,593,430 A | 1/1997 | Renger |
| 6,038,480 A | 3/2000 | Hrdlicka et al. |
| 6,473,653 B1 | 10/2002 | Schallhorn et al. |
| 6,859,667 B2 | 2/2005 | Goode |
| 6,978,178 B2 | 12/2005 | Sommer et al. |
| 7,214,189 B2 * | 5/2007 | Zdeblick ................ 600/300 |
| 2002/0169484 A1 | 11/2002 | Mathis et al. |
| 2003/0093130 A1 | 5/2003 | Stypulkowski |
| 2003/0120328 A1 | 6/2003 | Jenkins et al. |
| 2003/0149456 A1 | 8/2003 | Rottenberg et al. |
| 2005/0033370 A1 | 2/2005 | Jelen et al. |
| 2007/0027514 A1 | 2/2007 | Gerber |
| 2007/0027515 A1 | 2/2007 | Gerber |
| 2007/0043416 A1 | 2/2007 | Callas et al. |

* cited by examiner

*Primary Examiner* — Eric D. Bertram
(74) *Attorney, Agent, or Firm* — Shumaker & Sieffert, P.A.

(57) ABSTRACT

In general, the disclosure describes techniques for communication between at least one lead-borne device of an implantable lead and a medical device to which the lead is connected. The lead-borne device communicates with the medical device by modulating an impedance. The lead-borne device may communicate one or more bits of data to the medical device by selectively presenting either a first impedance or a second impedance to the medical device during one or more bit windows. The first and second impedance values may be respectively associated with first and second binary values, e.g., a high or one and low or zero.

31 Claims, 8 Drawing Sheets

COMMUNICATION BETWEEN A MEDICAL DEVICE AND A LEAD-BORNE DEVICE

TECHNICAL FIELD

The invention relates to implantable medical devices and, more particularly, implantable medical leads that comprise a device and are coupled to implantable medical devices.

BACKGROUND

Implantable and external medical devices are used for a variety of purposes related to treating or monitoring patients. For example, electrical stimulation is recognized as an effective therapy for patients with physical ailments such as chronic pain, movement disorders, gastrointestinal disorders, and pelvic floor disorders. Whether external or implanted, medical devices often deliver electrical stimulation to a patient or monitor the patient via a lead, which may be implanted within the patient.

Implantable leads may be used to place electrodes or sensors at a target location within the patient, e.g., proximate to target tissue, for delivery of stimulation or monitoring. Implantable leads include conductors that couple the electrodes or sensors, typically located near a distal end of the lead, to the medical device at the proximal end of the lead. Typically, leads include at least one conductor per electrode or sensor.

The complexity of leads, e.g., the number of electrodes per lead, has increased. Consequently, the number of conductors within the leads has increased. However, there are problems associated with increasing numbers of conductors within leads, including increased size, decreased flexibility, and an increased propensity for fracture of the conductors or other lead failure. Furthermore, increased numbers of conductors within the lead may increase the size of a header block on an implantable medical device, increasing its overall size, which may be undesirable for implantation.

Use of a switching device, sometimes referred to as a multiplexer (MUX), within the lead has been proposed as a way to avoid the problems associated with increasing numbers of conductors while providing increased numbers of electrodes or sensors on an implantable medical lead. A lead MUX may selectively, e.g., based on control signals from a medical device, couple a smaller number of proximal conductors to a greater number of distal conductors and associated electrodes or sensors. In this manner, the portion of the lead proximal of the MUX may have fewer conductors, and thereby avoid or lessen the problems associated with increased numbers of conductors. The lead MUX may be located relatively distally on the lead, so that a larger, proximal portion benefits from fewer conductors.

SUMMARY

In general, the invention provides techniques for communication between at least one device on, within, or carried by an implantable medical lead, i.e., an implantable medical lead-borne device, and a medical device to which the lead is connected. The lead-borne device may be a switching device or a multiplexer (MUX), for example. The lead-borne device communicates with the medical device by modulating an impedance. The lead-borne device may communicate one or more bits of data to the medical device by selectively presenting either a first impedance or a second impedance to the medical device during one or more bit windows. The first and second impedance values may be respectively associated with first and second binary values, e.g., a high or one and low or zero.

The medical device may measure impedance during the bit windows to decode the communication from the lead-borne device. For example, based on the impedance measured during a bit window, the medical device may determine whether that bit window contains a binary zero or one. The medical device may also check the validity of the communication, e.g., data, received from the lead-borne device based on the measured impedance.

In this manner, the lead-borne device may, for example, provide an ACK or NACK in response to a command from the medical device. An example of a command from the medical device is a command to couple certain distal lead conductors associated with certain electrodes or a sensor to proximal conductors within the lead, and thereby electrical couple the electrodes or sensor to the medical device. The lead-borne device may additionally or alternatively communicate data to the medical device, such as self-test results, error codes, or a sensed signal that has been converted to a digital signal.

In one embodiment, the invention is directed to an implantable medical lead comprising a lead body comprising a proximal end coupled to a medical device and a distal end, and a lead-borne device coupled to the implantable medical device by at least two conductors within the lead body. The lead-borne device selectively places either a first impedance associated with a first binary value or a second impedance associated with a second binary value across the at least two conductors and thereby communicates with the medical device.

In another embodiment, the invention is directed to a method performed by a lead-borne device of an implantable medical lead, the lead-borne device coupled to the implantable medical device by at least two conductors within the lead. The method comprises communicating with the medical device, wherein communicating with the medical device comprises selectively placing either a first impedance associated with a first binary value or a second impedance associated with a second binary value across the at least two conductors.

In another embodiment, the invention is directed to a system comprising a medical device, and an implantable medical lead. The implantable medical lead comprises a lead body comprising a proximal end coupled to the medical device and a distal end, and a lead-borne device coupled to the implantable medical device by at least two conductors within the lead body. The lead-borne device selectively places either a first impedance associated with a first binary value or a second impedance associated with a second binary value across the at least two conductors and thereby communicates with the medical device.

Embodiments of the invention may provide one or more advantages. For example, some embodiments utilize digital, e.g., binary, communication by modulating impedance between two values. Such embodiments may allow the lead-borne device to communicate responses or data that comprise multiple bits. Furthermore, because the communication from the lead-borne device to the medical device is by impedance modulation, the lead-borne device may more easily take the form of a passive device in some embodiments. Such embodiments may also avoid other problems with analog communication, such as the need for the medical device to more precisely measure impedance values.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
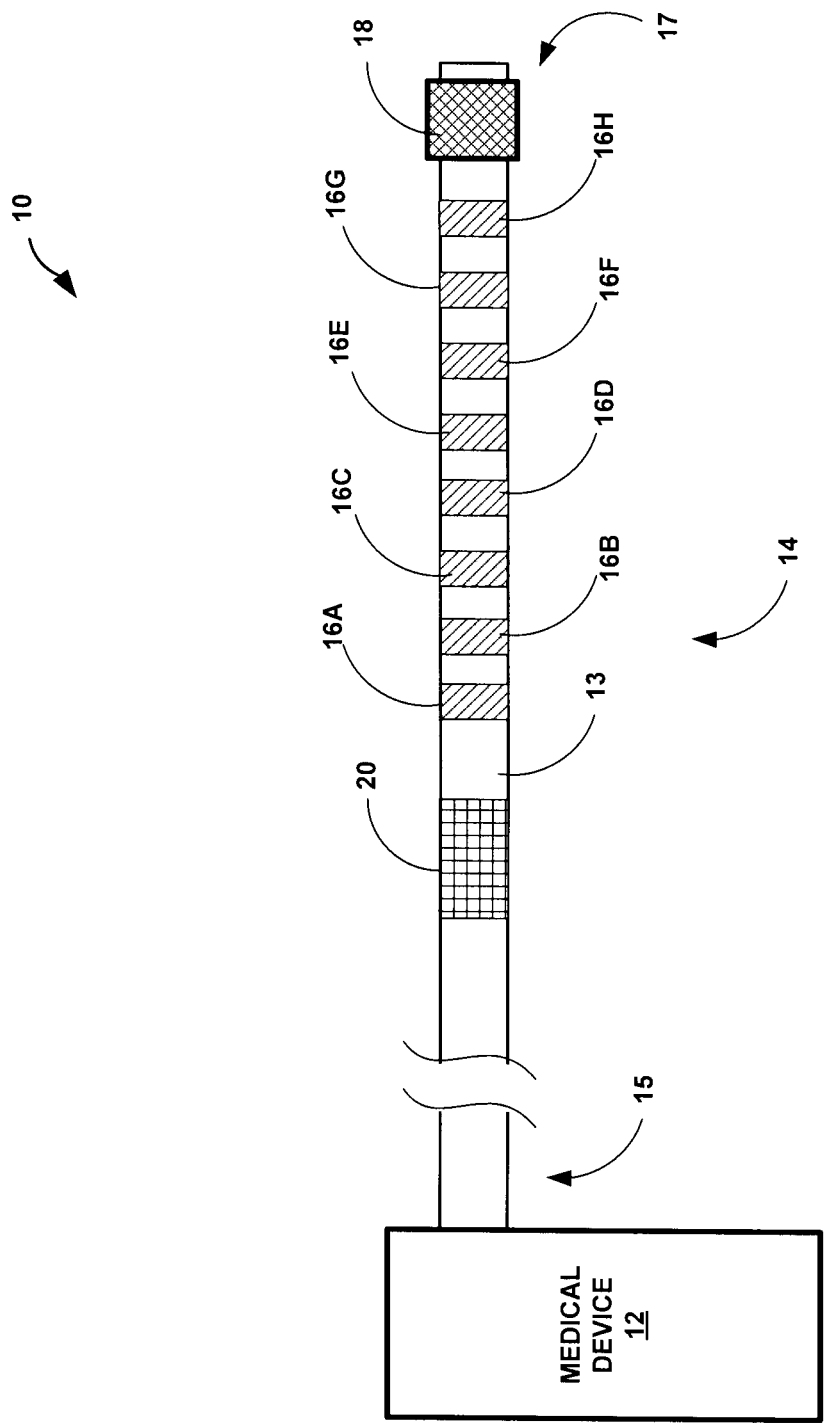
FIG. 1 is a conceptual diagram illustrating an example system in which a lead-borne device of an implantable medical lead communicates with a medical device.

FIG. 1 is a conceptual diagram illustrating an example system 10. In the illustrated example, system 10 includes a medical device 12 coupled to an implantable medical lead 14. Lead 14 includes a lead body 13 having a proximal end 15 that is coupled to medical device 12 and a distal end 17.

Lead 14 includes a plurality of electrodes 16A-16H (collectively "electrodes 16") near distal end 17 of lead body 13, e.g., on a distal portion of the lead. Medical device 12 may deliver stimulation to a patient (not shown) or sense physiological signals or parameters of the patient via electrodes 16. The number and type of electrodes 16 illustrated in FIG. 1 is merely an example. Embodiments may include one or more electrodes 16. Furthermore, electrodes 16 may take the form of ring electrodes, as illustrated in FIG. 1, or may have other shapes or configurations. For example, some embodiments may include electrodes 16 in the form of partial rings or ring segments, which are arranged at various circumferential and/or axial positions of the lead.

In the illustrated example, lead 14 also includes a sensor 18 near distal end 17 of lead body 13, e.g., on a distal portion of the lead. Sensor 18 may comprise, as examples, an activity sensor, a posture sensor, a pressure sensor, a flow sensor, an oxygen saturation sensor, a temperature sensor, a pH sensor, or a glucose sensor. Sensor 18 may comprise, as examples, an accelerometer, such as a multi-axis accelerometer, a strain gauge, a pressure sensitive-capacitor, an ultrasonic flow sensor, a thermistor, or an antimony electrode. Some embodiments may include multiple sensors and, in various embodiments, the one or more sensors may be positioned at locations of lead body 13 different than that illustrated in FIG. 1. Furthermore, although the illustrated example lead 14 includes electrodes 16 and a sensor 18, some embodiments may include only electrodes 16, or only one or more sensors 18.

Medical device 12 may be implantable or external. In systems where medical device 12 is external, lead body 13 may be connected percutaneously to medical device 12. Although only a single lead 14 is illustrated in the example of FIG. 1, systems according to the invention may include any number of leads. Medical device 12 may be used for one or both of delivering therapy to the patient or monitoring the patient. As examples, medical device may a cardiac pacemaker, cardiac defibrillator, or a neurostimulator, e.g., provide spinal cord stimulation, deep brain stimulation, or pelvic floor stimulation.

As illustrated in FIG. 1, lead 14 also includes a lead-borne device, which in the illustrated example takes the form of switching device, herein referred to as a multiplexer (MUX) 20, located proximally relative to electrodes 16 and sensor 18. As will be described in greater detail below, MUX 20 communicates with medical device 12 by modulating an impedance that is measured by medical device 12 between two values that are respectively associated with a binary one or zero. MUX 20 may communicate one or more bits of data to medical device 12 by selectively presenting either a first impedance or a second impedance to medical device 12 during one or more bit windows. Such embodiments may allow MUX 20 to communicate responses or data that comprise multiple bits.

Figure 2:
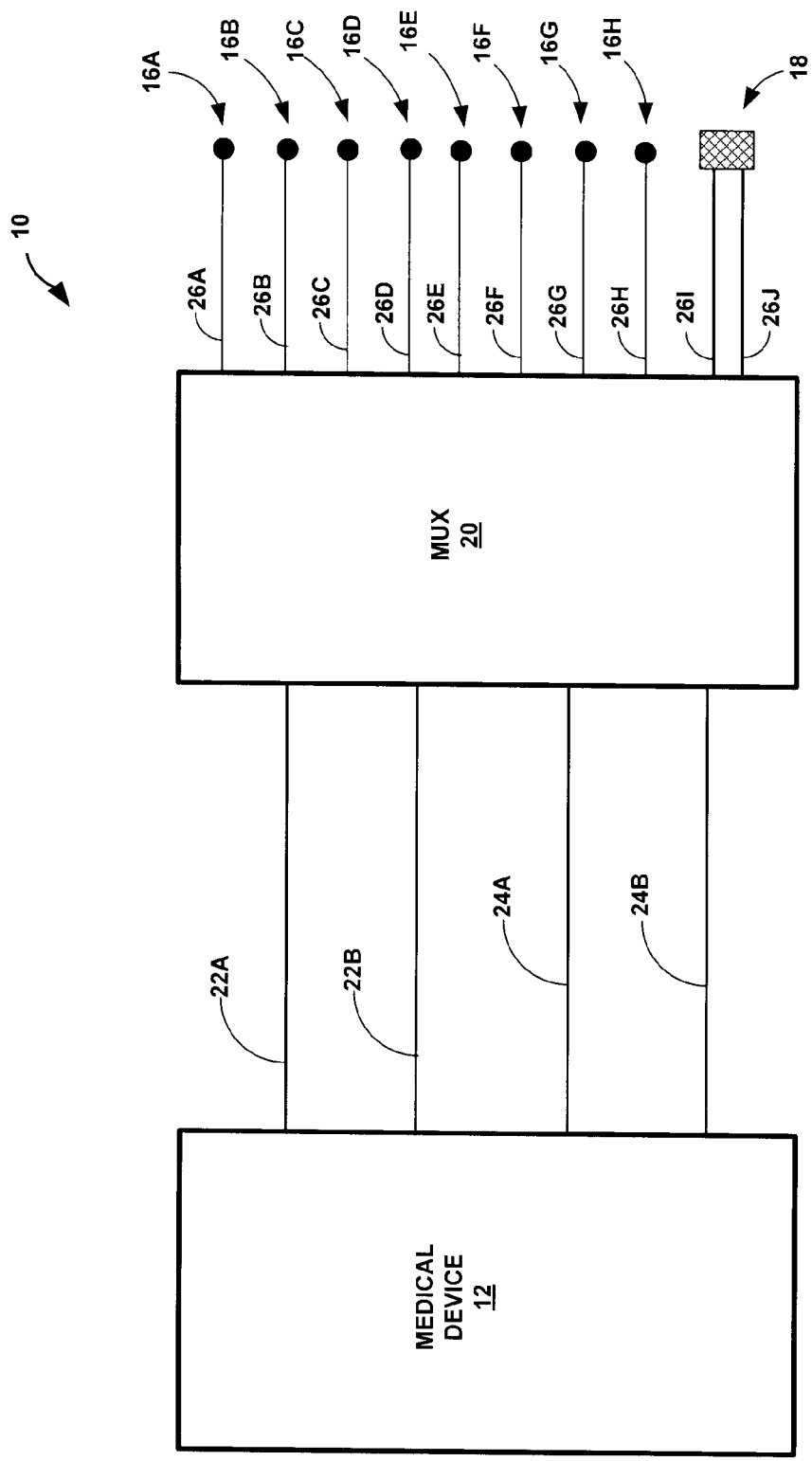
FIG. 2 is a block diagram further illustrating the example system of FIG. 1, including conductors within the implantable medical lead.

FIG. 2 is a block diagram further illustrating system 10. In particular, FIG. 2 illustrates an example configuration of conductors within lead body 13 of lead 14 (not shown in FIG. 2). As illustrated in the example of FIG. 2, medical device 12 is coupled to MUX by conductors 22A and 22B (collectively "conductors 22"), and conductors 24A and 24B (collectively "conductors 24"). MUX 20 is coupled to electrodes 16A-16H by respective conductors 26A-26H, and to sensor 18 by conductors 26I and 26J.

Conductors 22 and 24 may collectively be referred to as a first proximal plurality of conductors within lead body 13, and conductors 26A-26J (collectively "conductors 26") may be referred to as a second distal plurality of conductors within the lead body. In the illustrated example, the first proximal plurality of conductors 22 and 24 has fewer conductors than the second distal plurality of conductors 26. The use of MUX 20 facilitates such an arrangement of conductors, which may allow the proximal portion of lead 14 to be thinner and more flexible than a lead with a similar number of electrodes/sensors that did not include a MUX and instead had dedicated conductors for each electrode/sensor extending throughout the length of the lead. Fewer proximal conductors 22 and 24 may also allow a smaller connector block on medical device 12 for accommodating the connection of the conductors to circuitry within medical device 12.

In the illustrated example, conductors 22 comprise a communication line and a ground line. MUX 20 communicates with medical device 12 via conductors 22. In some embodiments, MUX 20 also receives operational power from medical device 12 via conductors 22. In some embodiments, MUX 20 is a passive device that receives substantially all of its operational power from medical device 12.

Conductors 24 are signal lines by which medical device 12 may deliver signals, e.g., electrical stimulation, to electrodes 16, and/or receive signals from electrodes 16 or sensor 20, via MUX 20. MUX 20 couples conductors 24 to a selected plurality of conductors 26. MUX 20 may couple conductors 24 to selected conductors 26 based on programming data or commands received from medical device 12 via conductors 22. In this manner, medical device 12 may, for example, control through which of electrodes 16 electrical stimulation is delivered or a signal sensed. In this manner, medical device 12 may also control when a signal is received from sensor 18. Medical device 12 may send programming data as often as desired to control MUX to change which of conductors 26 are coupled to conductors 24, e.g., to change which of electrodes 16 are selected for delivery of stimulation.

Although the proximal plurality of conductors 22 and 24 is illustrated as including four conductors, the invention is not so limited. For example, the proximal plurality of conductors may include additional signal conductors 24 that may, for example, be used by medical device 12 to provide multiple channels of electrical stimulation. In some embodiments, the proximal plurality of conductors may include fewer than four conductors. In some embodiments, power/communication conductors 22 and signal conductors 24 may share a common ground line. In other embodiments, power, communication and signals, e.g., stimulation or sensed signals, may be multiplexed on a common pair of conductors between medical device 12 and MUX 20.

Figure 3:
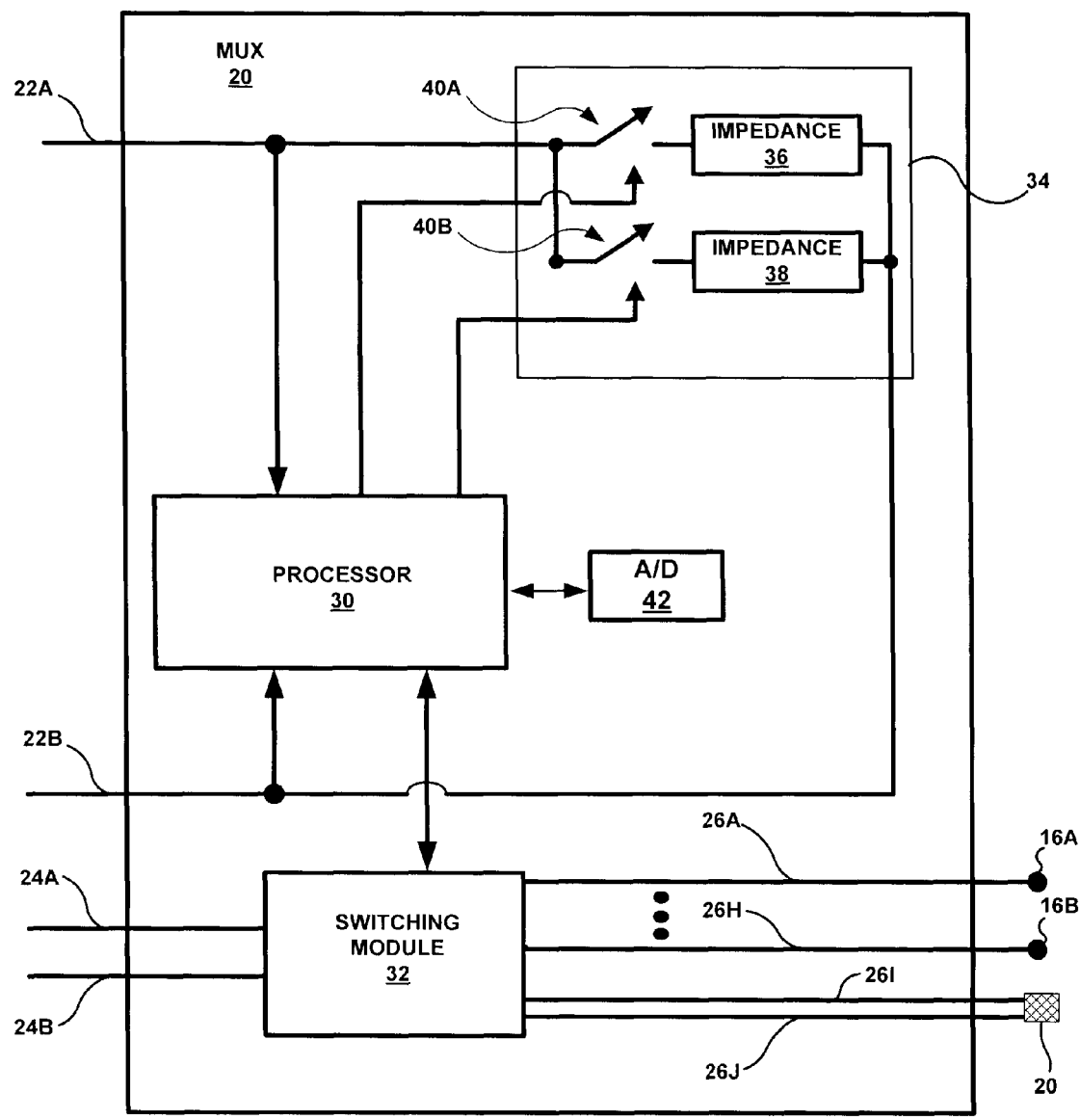
FIG. 3 is a block diagram further illustrating an example configuration of the lead-borne device of the system of FIG. 1.

FIG. 3 is a block diagram illustrating an example configuration of MUX 20. In the illustrated example, MUX 20 includes a processor 30, a switching module 32, and an impedance modulation module 34. Switching module 32 is connected on one side to conductors 24 from medical device 12, and on another side to conductors 26 from electrode 16 and sensor 18. Processor 30 controls switching module 32 to couple conductors 24 to selected ones of conductors 26. Processor 30 may control switching module 32 based on programming data or commands received from medical device 12 via conductors 22. Switching module 32 may comprise a plurality transistors or other switches controllable by processor 30. Processor 30 may comprise, as examples, a microprocessor, application specific integrated circuit (ASIC), field programmable gate array (FPGA), or other logic circuitry.

Processor 30 may also send a communication to medical device 12 via conductors 22. For example, processor 30 may provide an ACK or NACK in response to programming data from medical device 12, such a programming data regarding the configuration of switching module 32. Processor 30 may also perform self-diagnostic tests for MUX 20, e.g., testing or monitoring the performance of processor 30 and/or the other components of MUX 20. Processor 30 may communicate a result of such a self-test to medical device 12. The communicated self-test result may comprise, for example, an error code. Furthermore, in some embodiments, as illustrated in FIG. 3, MUX 20 may comprise an analog-to-digital (A/D) converter 42, which may convert analog signals from electrodes 16 or sensor 18 to digital signals. Processor 30 may communicate such digital signals to medical device 12.

MUX 20 communicates with medical device 12 via communication conductors 22. More particularly, processor 30 communicates with medical device 12 by controlling impedance modulation module 34 to modulate an impedance across conductors 22. In the illustrated example, processor 30 controls impedance modulation module 34 to place either a first impedance 36 or a second impedance 38 across conductors 22 by controlling switches 40A and 40B (collectively "switches 40").

Switches 40 may comprise transistors, and impedances 36 and 38 may comprise resistors. However, the invention is not limited to these examples. Furthermore, impedance modulation module 34 may include more than two switches and more than two circuit elements that provide impedance in order to selectively place one of two impedances across conductors 22.

Impedances 36 and 38 are respectively associated with a binary value of low, or zero, and a binary value of high, or one. In order to communicate a bit of information, i.e., to communicate a one or a zero to medical device, processor 30 controls module 34 to selectively place either impedance 36 or impedance 38 across conductors 22 during a bit window. Processor 30 may communicate one or more bits of information by placing either impedance 36 or impedance 38 across conductors 22 during one or more bit windows. In this manner MUX 20 may send communications comprising multiple bits of sensor or other data to medical device 12.

Processor 30 may maintain synchronization with a processor of medical device 12, and both processors may be programmed such that communication from processor 30 is properly understood by medical device 12, e.g., such that both processors commonly recognize the beginning and end of the one or more bit windows. During each of the bit windows, medical device 12 may place one or more pulses or other signals on conductors 22 in order to measure impedance, and thereby detect which of impedances 36 and 38 processor 30 has placed across the conductors. In this manner, medical device 12 may determine whether processor 30 is communicating a zero or a one during a particular bit window. The pulses or other signals used for impedance measurement may also serve other purposes. For example, such pulses or signals may be a source of operational power for MUX 20. MUX 20 may include circuitry (not shown) to capture and/or store energy from such pulses for the purpose of powering MUX 20, e.g., a capacitor, battery, rectifier, or the like.

Figure 4:
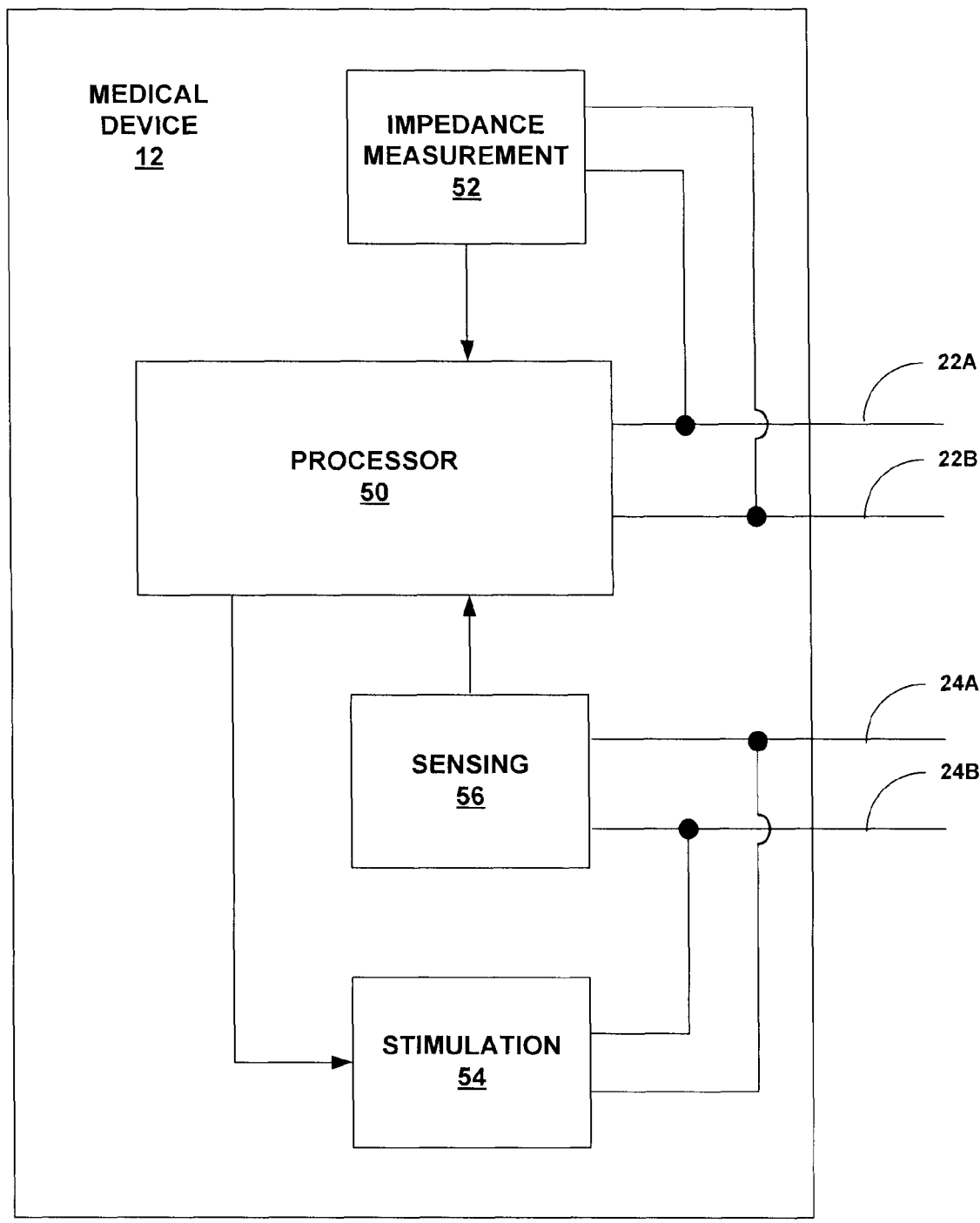
FIG. 4 is a block diagram further illustrating an example configuration of the medical device of the system of FIG. 1.

FIG. 4 is a block diagram further illustrating an example configuration of medical device 12. In the illustrated example, medical device 12 includes a processor 50, impedance measurement module 52, stimulation module 54 and sensing module 56. Medical device 12 may include more components not illustrated in FIG. 4, but known in the art, such as a power source, memory, and telemetry circuitry. Some embodiments do not include both stimulation module 54 and sensing module 56.

Processor 50 may comprise any one or more of a microprocessor, ASIC, FPGA, digital signal processor (DSP), or other logic circuitry. Processor 50 sends programming data, e.g., to control the configuration of switching module 32 (FIG. 3), to MUX 20 via communication conductors 22. The communication from processor 50 to MUX 20 may be digital communication by modulation of voltage on conductors 22.

Processor 50 also receives communications from MUX 20, as described above, based on an impedance placed on conductors 22 by the MUX. Processor 50 may place voltage or current pulses (or other continuous time signals) on conductors, or control a signal generator to place the signals on conductors, so that the impedance on conductors 22 may be measured by impedance measurement module 52. Module 52 provide an indication of the measured impedance to processor 50, which determines a binary value that was communicated by MUX 20 based on the indication. Impedance measurement module 52 may comprise any known circuitry for measuring impedance.

Stimulation module 54 and sensing module 56 are coupled to MUX 20 via signal conductors 24. Based on the configuration of switching module 32 processor 50 may control stimulation module 54 to deliver electrical stimulation, e.g., pulses or other signals, to a patient via a selected plurality of electrodes 16. Based on the configuration of switching module 32 processor 50 may receive signals sensed by a selected plurality of electrodes 16 or sensor 18 via sensing module 56. Sensing module 56 may comprise circuitry to condition the signals received via conductors 24, such as one or more amplifiers or filters, or an analog-to-digital converter.

Figure 5:
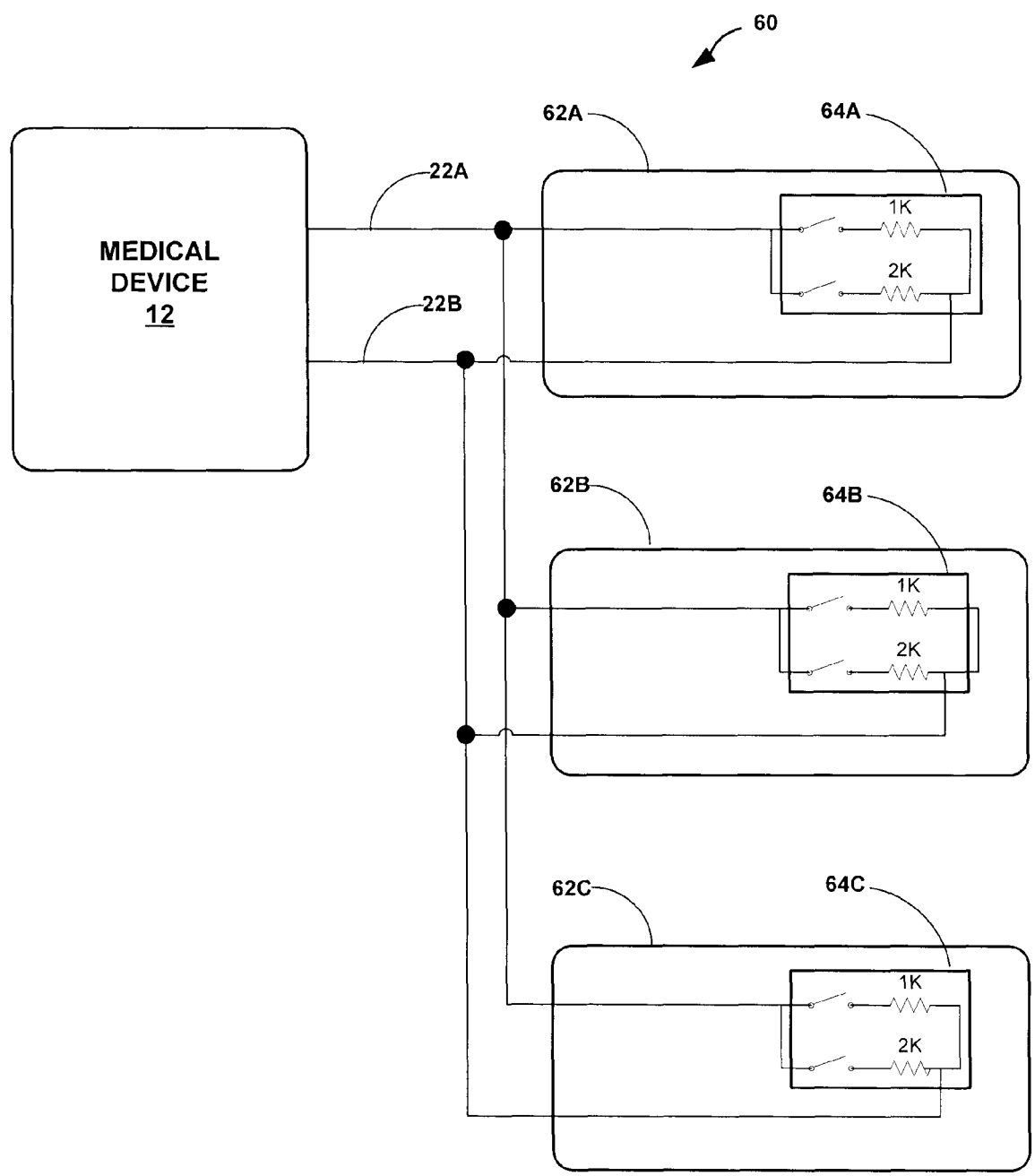
FIG. 5 is a block diagram illustrating another example system in which a plurality of lead-borne devices of an implantable medical lead communicate with a medical device.

FIG. 5 is a block diagram illustrating another example system 60 in which an implantable lead (not shown) comprises a plurality of MUXs 62A-62C (collectively "MUXs 62") that communicate with a medical device 12 coupled to the lead. The illustrated example includes three MUXs. However, other embodiments may include greater or fewer MUXs. For ease of illustration, conductors 24, as well as various elements of MUXs 62 illustrated with respect to MUX 20 in FIG. 3, are not shown in FIG. 5.

MUXs 62 may each be coupled to conductors 22 and 24, i.e., the first proximal plurality of conductors. MUXs 62 may be coupled to conductors 22 and 24 in parallel, as illustrated in FIG. 5 with respect to conductors 22. Although not shown in FIG. 5, each of MUXs 62 may be coupled to respective electrodes 16 or sensors 18 via a respective second distal plurality of conductors 26.

Medical device 12, e.g., processor 50 of the medical device, sends programming data or other communication to MUXs 62 by modulating a voltage or current on conductors 22. Medical device 12 may address MUXs 62, e.g., by including a code associated with one of MUXs 62 in a communication intended for the MUX. Each of MUXs 62 includes a respective one of impedance modulation modules 64A-64C (collectively "impedance modulation modules 64") for sending a communication to medical device 12 in the manner discussed above with respect to MUX 20 and FIG. 3. In the illustrated example, each of modules 64 includes a first impedance of 1000 ohms and a second impedance of 2000 ohms. The illustrated impedance values are merely examples.

Medical device 12, e.g., processor 50 of the medical device, may determine whether a communication from one of MUXs 62 is valid based on the measured impedance. For example, medical device 12 may determine whether the measured impedance is at or within a range around an expected value that reflects the placement of either of 1000 or 2000 ohms across conductors 22 by one of MUXs 62. One situation in which a communication may not be valid is where two or more of MUXs 62 place an impedance across conductors 22 at the same time, i.e., communications from two or more MUXs on the common bus "collide." In such situations, the impedance on conductors 22 measured by medical device 12 may be identifiable by medical device 12 as invalid. For example, if MUX 62A places 1000 ohm across conductors 22, and MUX 62B places 2000 ohm across the conductors, the two impedances in parallel are equivalent to one 666 ohm impedance. Medical device 12 may detect such an impedance as being indicative of an invalid communication from whichever of MUXs 62A and 62B was expected to send a communication.

Figure 6A:
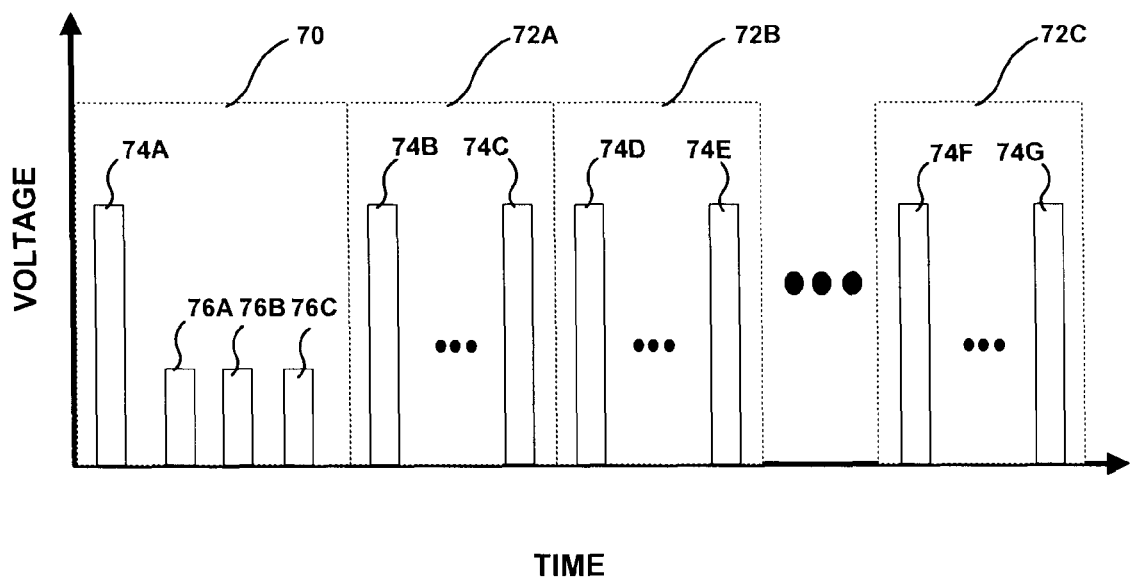
FIGS. 6A and 6B are timing diagrams illustrating an example technique for communication between a medical device and a lead-borne device.
Figure 6B:
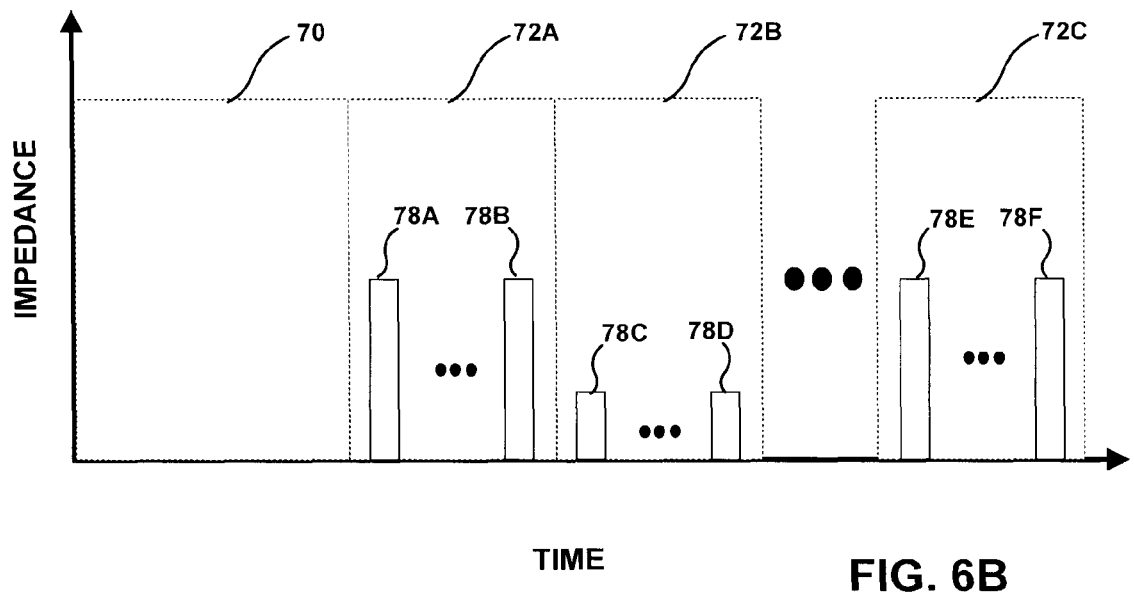

FIGS. 6A and 6B are timing diagrams illustrating an example technique for communication between medical device 12 and a lead MUX, e.g., MUX 20. FIG. 6A illustrates voltage over time, which FIG. 6B illustrates impedance on conductors 22 as measured by medical device 12 over the same time period. The illustrated time period includes a programming window 70, during which medical device 12 communicates with MUX 20, and a series of bit windows 72A-72C, during which MUX 20 communicates with medical device 12, e.g., in response to the command or data from the medical device.

As illustrated in FIG. 6A, medical device 12 may place a plurality of pulses 74A-74G on conductors 22, both during the programming window 70, and within each of the bit windows 72. In some embodiments, pulses 74A-74G are power pulses (collectively "power pulses 74") that provide operational power to MUX 20. Additionally, medical device 12 may use pulses 74B-74G that occur during bit windows 72 to measure the impedance on conductors 22, and thereby decode communicated bits from MUX 20. FIG. 6A also illustrates programming pulses 76A-76C from medical device 12 to MUX during programming window 70. Programming pulses 76A-76C may, for example, instruct MUX 20 to couple selected electrodes 16 to the medical device.

FIG. 6B illustrates impedances 78A-78F (collectively "impedances 78") measured by medical device 12 on conductors 22 within bit windows 72. As illustrated by FIGS. 6A and 6B, medical device 12 measures impedances 78 during and based on the delivery of pulses 74B-74G on conductors 22. As illustrated in FIGS. 6A and 6B, medical device 12 may deliver a plurality of pulses 74 and measure a plurality of impedances 78 during each bit window 72, to increase the likelihood that medical device 12 will properly interpret or decode the binary value of the bit conveyed by MUX 20 for that bit window. As illustrated in the example of FIG. 6B, medical device 12 measures a high impedance value during bit windows 72A and 72C, and a low impedance value during bit window 72B. Thus, the binary values communicated by MUX 20 during these bit window may be one, zero and one, respectively. The numbers of bit windows 72, pulses 74 and 76, and impedance measurements 78 illustrated in FIGS. 6A and 6B are merely examples.

Figure 7:
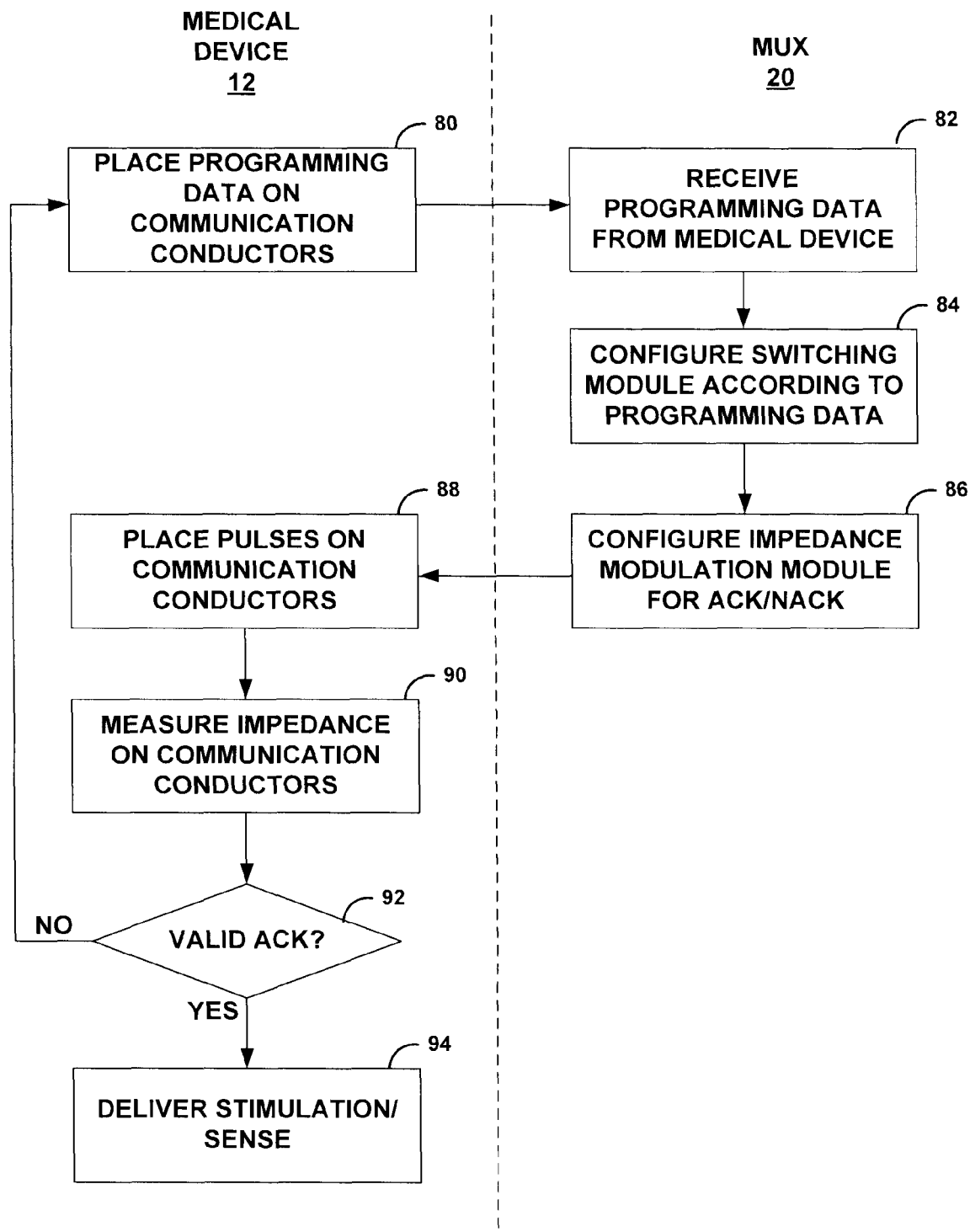
FIG. 7 is a flow diagram illustrating an example technique for communication between a medical device and a lead-borne device.

FIG. 7 is a flow diagram illustrating an example technique for communication between a medical device and a lead MUX, which will be described with reference to system 10 as described above. According to the example technique, medical device 12 places programming data on communication conductors 22 (80). MUX 20 receives the programming data from medical device 12 (82). MUX 20 configures switching module 32 according to the programming data to, for example, couple selected electrodes 16, or sensors 18 to medical device 12 (84).

MUX 20 may also configure impedance modulation module 34 to provide an ACK/NACK to medical device 12 in response to the programming data (86), which may indicate to medical device 12 whether the programming data was received and acted on by MUX 20. The ACK/NACK may comprise one or more bits and, therefore, MUX 20 may configure/reconfigure impedance modulation module 34 a number of times for a number of different bit windows 72.

During the one or more bit windows, medical device 12 places one or more pulses or other signals, e.g., power pulses 74, on conductors 22 (88), and measures the impedance on the conductors (90). Based on the measured impedance(s), medical device 12 determines whether MUX 20 has communicated a valid ACK in response to the programming data (92). If MUX 20 has not communicated a valid ACK, medical device 12 may resend the programming data (80). If MUX 20 has communicated a valid ACK, medical device 12 may deliver electrical stimulation or sense signals via the selected electrodes 16 or sensors 18 (94).

Figure 8:
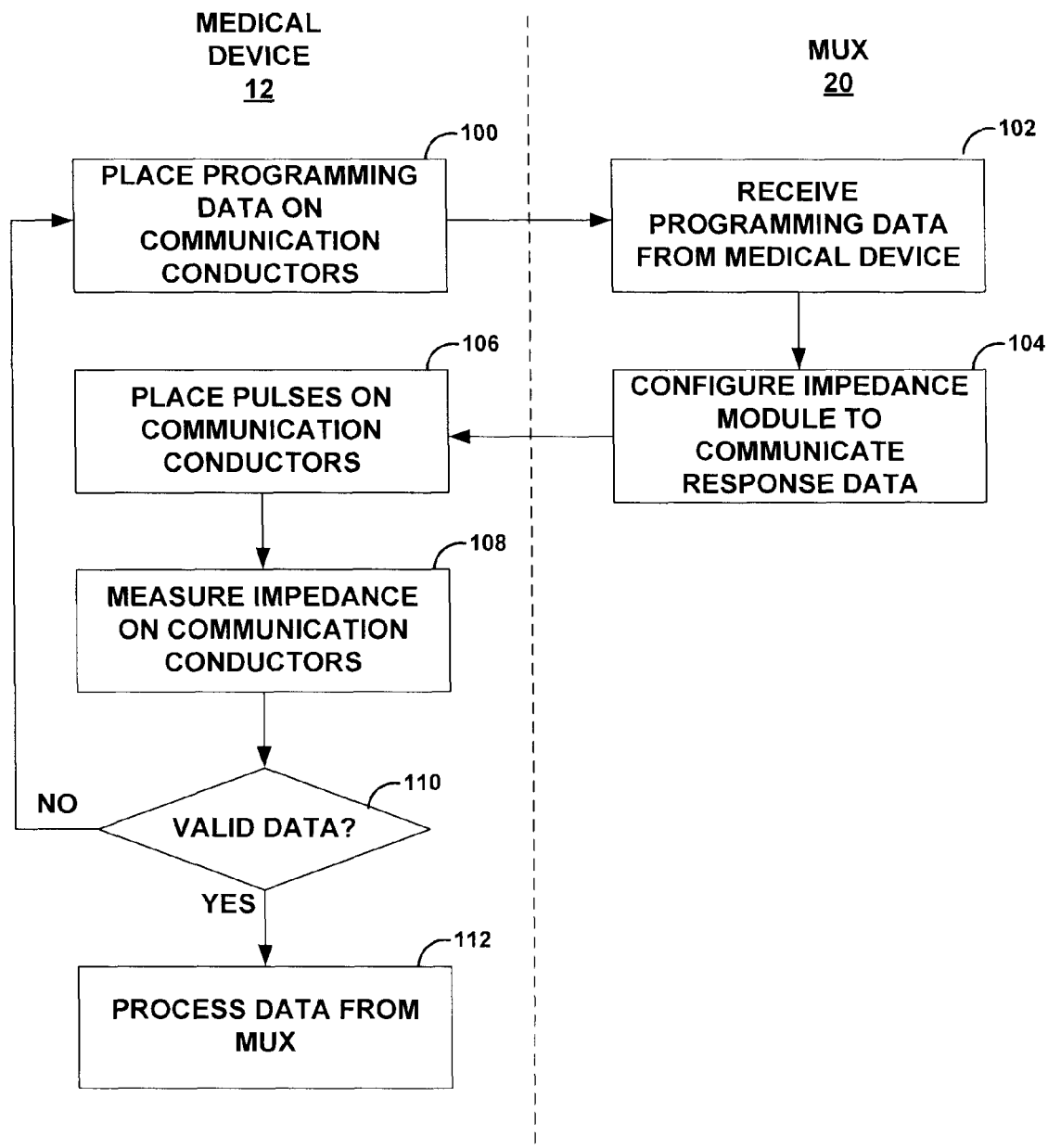
FIG. 8 is a flow diagram illustrating another example technique for communication between a medical device and a lead-borne device.

FIG. 8 is a flow diagram illustrating another example technique for communication between a medical device and a lead MUX, which will be described with reference to system 10 as described above. As illustrated by FIG. 8, MUX 20 may communicate data other than an ACK/NACK in some embodiments of the invention.

According to the example technique, medical device 12 places programming data on communication conductors 22 (100). In this example, programming data may be a request for data from medical device 12 to MUX 20. For example, medical device 12 may request self-test data or a digital sensed signal from the MUX 20.

MUX 20 receives the programming data from medical device 12 (102). MUX 20 configures impedance modulation module 34 to communicate a response, e.g., response data, to medical device 12 in response to the programming data (104).

The response data may comprise one or more bits and, therefore, MUX 20 may configure/reconfigure impedance modulation module 34 a number of times for a number of different bit windows 72.

During the one or more bit windows, medical device 12 places one or more pulses or other signals, e.g., power pulses 74, on conductors 22 (106), and measures the impedance on the conductors (108). Based on the measured impedance(s), medical device 12 determines whether MUX 20 has communicated a valid data in response to the programming data (110). If MUX 20 has not communicated valid data, medical device 12 may resend the programming data (100). If MUX 20 has communicated valid data, medical device 12 may process the data (112).

Various embodiments of the invention have been described. However, one of ordinary skill in the art will appreciate that various modifications may be made to the described embodiments without departing from the scope of the claimed invention. For example, although embodiments in which a lead-borne device comprises a MUX are described herein, the invention is not so limited. A lead-borne device may be any switching device that selectively couples a first, proximal plurality of conductors within a lead to a second, proximal plurality of conductors within a lead. Furthermore, a lead-borne device is not limited to devices that perform this function. Any device on, within or carried by an implantable medical lead, e.g., any lead-borne device, which may comprise elements for switching, sensing, therapy, analog-to-digital conversion, or any other function, may communicate with a medical device to which the implantable medical lead is coupled according to the techniques described herein. These and other embodiments are within the scope of the following claims.

The invention claimed is:

1. An implantable medical lead comprising:
    a lead body comprising a proximal end coupled to a medical device and a distal end;
    a lead-borne device coupled to the medical device by at least two conductors within the lead body, wherein the lead-borne device selectively places either a first impedance associated with a first binary value or a second, different impedance associated with a second, different binary value across the at least two conductors to communicate the first binary value or the second binary value to the medical device.

2. The implantable medical lead of claim 1, wherein, during each of a plurality of bit windows, the lead-borne device selectively places either the first impedance or the second impedance across the at least two conductors to communicate a plurality of bits of data that include the first binary value and the second binary value to the medical device.

3. The implantable medical lead of claim 1, wherein the lead-borne device selectively places either the first impedance or the second impedance across the at least two conductors to communicate at least one of a self test result or an error code to the medical device.

4. The implantable medical lead of claim 1,
    wherein the lead-borne device comprises an analog-to-digital converter that receives a sensed analog signal and converts the sensed analog signal to a digital signal, and wherein the lead-borne device selectively places either the first impedance or the second impedance across the at least two conductors to communicate the digital signal to the medical device.

5. The implantable medical lead of claim 1, further comprising at least one additional lead-borne device coupled to the medical device by the at least two conductors within the lead body,
    wherein the additional lead-borne device selectively places either the first impedance associated with the first binary value or the second impedance associated with the second binary value across the at least two conductors to communicate with the medical device.

6. The implantable medical lead of claim 1, further comprising:
    a first proximal plurality of conductors within the lead body connected to the medical device at the proximal end of the lead body, the first proximal plurality of conductors comprising the at least two conductors; and
    a second distal plurality of conductors within the lead body; and
    wherein the lead-borne device selectively couples conductors from the first proximal plurality of conductors to conductors from the second distal plurality of conductors.

7. The implantable medical lead of claim 6, wherein the lead-borne device receives programming data from the medical device via the at least two conductors, selectively couples the conductors from the first proximal plurality of conductors to the conductors from the second distal plurality of conductors according to the programming data, and selectively places either the first impedance or the second impedance across the at least two conductors to acknowledge the programming data from the medical device.

8. The implantable medical lead of claim 6, further comprising a plurality of electrodes, each of the electrodes coupled to the lead-borne device by a respective one of the second distal plurality of conductors, wherein the lead-borne device selectively couples the second distal plurality of conductors to conductors from the first proximal plurality of conductors and thereby couples electrodes selected from the plurality of electrodes to the medical device.

9. The implantable medical lead of claim 6, further comprising a sensor coupled to the lead-borne device by at least two of the distal plurality of conductors, wherein the lead-borne device selectively couples the at least two of the second distal plurality of conductors to conductors from the first proximal plurality of conductors and thereby couples the sensor to the medical device.

10. The implantable medical lead of claim 6, wherein the lead-borne device comprises at least one of a switching module or a multiplexer.

11. A method performed by a lead-borne device of an implantable medical lead, the lead-borne device coupled to a medical device by at least two conductors within the lead, the method comprising:
    communicating with the medical device, wherein communicating with the medical device comprises selectively placing either a first impedance associated with a first binary value or a second, different impedance associated with a second, different binary value across the at least two conductors to communicate the first binary value or the second binary value to the medical device.

12. The method of claim 11, wherein communicating with the medical device comprises communicating a plurality of bits of data that include the first binary value and the second binary value to the medical device, and wherein selectively placing either a first impedance or a second impedance across the at least two conductors comprises, during each of a plurality bit windows, selectively placing either the first impedance or the second impedance across the at least two conductors to communicate the plurality of bits of data to the medical device.

13. The method of claim 11, wherein communicating with the medical device comprises communicating at least one of a self test result or an error code to the medical device.

14. The method of claim 11, further comprising:
receiving a sensed analog signal; and
converting the sensed analog signal to a digital signal,
wherein communicating with the medical device comprises communicating the digital signal to the medical device.

15. The method of claim 11, further comprising selectively coupling conductors from a first proximal plurality of conductors to conductors from a second distal plurality of conductors, wherein the first plurality of conductors is connected to a medical device and comprises the at least two conductors.

16. The method of claim 15,
further comprising receiving programming data from the medical device via the at least two conductors,
wherein selectively coupling conductors comprises selectively coupling the conductors from the first proximal plurality of conductors to the conductors from the second distal plurality of conductors according to the programming data, and
wherein communicating with the medical device comprises acknowledging the programming data from the medical device.

17. The method of claim 15,
wherein the lead comprises a plurality of electrodes, each of the electrodes coupled to the lead-borne device by a respective one of the second distal plurality of conductors, and
wherein selectively coupling conductors comprises selectively coupling electrodes selected from the plurality of electrodes to the medical device.

18. The method of claim 15,
wherein the lead comprises a sensor coupled to the lead-borne device by at least two of the distal plurality of conductors, and
wherein selectively coupling conductors comprises selectively coupling the sensor to the medical device.

19. The method of claim 11, wherein the medical device comprises an implantable medical device.

20. A system comprising:
a medical device; and
an implantable medical lead that comprises:
a lead body comprising a proximal end coupled to the medical device and a distal end, and
a lead-borne device coupled to the medical device by at least two conductors within the lead body, wherein the lead-borne device selectively places either a first impedance associated with a first binary value or a second, different impedance associated with a second, different binary value across the at least two conductors to communicate the first binary value or the second binary value to the medical device.

21. The system of claim 20, wherein, during each of a plurality of bit windows, the lead-borne device selectively places either the first impedance or the second impedance across the at least two conductors to communicate a plurality of bits of data to the medical device.

22. The system of claim 20, wherein, during each of one or more bit windows, the medical device measures an impedance on the at least two conductors and identifies the first or second binary value based on the measured impedance to receive communication from the lead-borne device.

23. The system of claim 22,
wherein during each of the one or more bit windows, the medical device delivers one or more power pulses to the lead-borne device via the at least two conductors,
wherein the power pulses provide operational power for the lead-borne device, and
wherein the medical device measures the impedance on the at least two conductors during the delivery of the power pulses and identifies the first or second binary value based on the measured impedance.

24. The system of claim 22, wherein the medical device determines whether the communication from the lead-borne device is valid based on the measured impedance.

25. The system of claim 20,
wherein the implantable medical lead further comprises at least one additional lead-borne device within the lead body coupled to the medical device by the at least two conductors within the lead body,
wherein the additional lead-borne device selectively places either the first impedance associated with the first binary value or the second impedance associated with the second binary value across the at least two conductors to communicate with the medical device.

26. The system of claim 25,
wherein each of the lead-borne devices places either the first impedance or the second impedance across the at least two conductors at approximately the same time, and
wherein the medical device measures impedance across the at least two conductors to determine whether the communication from the lead-borne devices is invalid.

27. The system of claim 20, wherein the implantable medical lead further comprises:
a first proximal plurality of conductors within the lead body connected to the medical device at the proximal end of the lead body, the first proximal plurality of conductors comprising the at least two conductors; and
a second distal plurality of conductors within the lead body, and
wherein the lead-borne device selectively couples conductors from the first proximal plurality of conductors to conductors from the second distal plurality of conductors.

28. The system of claim 27, wherein the lead-borne device receives programming data from the medical device via the at least two of the first proximal plurality of conductors, selectively couples the conductors from the first proximal plurality of conductors to the conductors from the second distal plurality of conductors according to the programming data, and selectively places either the first impedance or the second impedance across the at least two conductors to acknowledge the programming data from the medical device.

29. The system of claim 27, wherein the implantable medical lead further comprises a plurality of electrodes, each of the electrodes coupled to the lead-borne device by a respective one of the second distal plurality of conductors, wherein the lead-borne device selectively couples the second distal plurality of conductors to conductors from the first proximal plurality of conductors and thereby couples electrodes selected from the plurality of electrodes to the medical device.

30. The system of claim 27, wherein the medical device at least one of delivers stimulation to a patient or senses a physiological signal via the selected electrodes.

31. The system of claim 20, wherein the medical device comprises an implantable medical device.

* * * * *